United States Patent
Ofstead et al.

(10) Patent No.: US 8,129,159 B2
(45) Date of Patent: Mar. 6, 2012

(54) ATTACHMENT OF MOLECULES TO SURFACES

(75) Inventors: Ronald F. Ofstead, Maplewood, MN (US); Melvin J. Swanson, Carver, MN (US); Dale G. Swan, St. Louis Park, MN (US)

(73) Assignee: Surmodics, Inc., Eden Prairie, MN (US)

( * ) Notice: Subject to any disclaimer, the term of this patent is extended or adjusted under 35 U.S.C. 154(b) by 0 days.

(21) Appl. No.: 12/878,236

(22) Filed: Sep. 9, 2010

(65) Prior Publication Data

US 2011/0009292 A1 Jan. 13, 2011

Related U.S. Application Data

(62) Division of application No. 11/901,033, filed on Sep. 14, 2007, now Pat. No. 7,829,317, and a division of application No. 10/677,022, filed on Oct. 1, 2003, now Pat. No. 7,309,593.

(51) Int. Cl.
*C12N 1/00* (2006.01)
*C12N 11/16* (2006.01)
*C40B 40/00* (2006.01)
*C12Q 1/00* (2006.01)
*C12Q 1/70* (2006.01)
*C12Q 1/68* (2006.01)
*C12Q 33/53* (2006.01)

(52) U.S. Cl. ..................... 435/174; 435/4; 435/5; 435/6; 435/7.1; 435/7.2; 506/13; 506/15; 506/16

(58) Field of Classification Search ................. 435/4, 5, 435/6, 7.1, 7.2, 174; 506/13, 15, 16
See application file for complete search history.

(56) References Cited

U.S. PATENT DOCUMENTS

| | | | |
|---|---|---|---|
| 4,542,102 A | 9/1985 | Dattagupta et al. |
| 4,582,860 A | 4/1986 | Bigwood et al. |
| 4,722,906 A | 2/1988 | Guire |
| 4,973,493 A | 11/1990 | Guire |
| 4,979,959 A | 12/1990 | Guire |
| 5,002,582 A | 3/1991 | Guire et al. |
| 5,217,492 A | 6/1993 | Guire et al. |
| 5,414,075 A | 5/1995 | Swan et al. |
| 5,510,084 A | 4/1996 | Cros et al. |
| 5,512,329 A | 4/1996 | Guire et al. |
| 5,512,474 A | 4/1996 | Clapper et al. |

(Continued)

FOREIGN PATENT DOCUMENTS

DE 198 04 518 A1 8/1999

(Continued)

OTHER PUBLICATIONS

Beaucage, Serge L., "Strategies in the Preparation of DNA Oligonucleotide Arrays for Diagnostic Applications", *Current Medicinal Chemistry*, vol. 8 2001, 1213-1244.

(Continued)

*Primary Examiner* — Jezia Riley
(74) *Attorney, Agent, or Firm* — Pauly, Devries, Smith & Deffner, L.L.C.

(57) ABSTRACT

The present invention relates to methods, reagents, and substrates that can be used for, for example, immobilizing biomolecules, such as nucleic acids and proteins. In an embodiment, the present invention relates to surfaces coated with a polymer according to the present invention. In an embodiment, the present invention relates to methods for thermochemically and/or photochemically attaching molecules to a surface at a high density.

9 Claims, 1 Drawing Sheet

CodeLink Activated slide

Coated with Compound $V_B$

U.S. PATENT DOCUMENTS

| | | | |
|---|---|---|---|
| 5,563,056 | A | 10/1996 | Swan et al. |
| 5,580,697 | A | 12/1996 | Keana et al. |
| 5,610,287 | A | 3/1997 | Nikiforov et al. |
| 5,637,460 | A | 6/1997 | Swan et al. |
| 5,643,580 | A | 7/1997 | Subramaniam |
| 5,654,162 | A | 8/1997 | Guire et al. |
| 5,707,818 | A | 1/1998 | Chudzik et al. |
| 5,714,360 | A | 2/1998 | Swan et al. |
| 5,718,726 | A | 2/1998 | Amon et al. |
| 5,741,551 | A | 4/1998 | Guire et al. |
| 5,744,515 | A | 4/1998 | Clapper |
| 5,783,502 | A | 7/1998 | Swanson |
| 5,858,653 | A | 1/1999 | Duran et al. |
| 5,942,555 | A | 8/1999 | Swanson et al. |
| 5,981,734 | A | 11/1999 | Mirzabekov et al. |
| 6,057,100 | A | 5/2000 | Heyneker |
| 6,254,634 | B1 | 7/2001 | Anderson et al. |
| 6,410,044 | B1 | 6/2002 | Chudzik et al. |
| 6,465,178 | B2 | 10/2002 | Chappa et al. |
| 7,309,593 | B2 | 12/2007 | Ofstead et al. |
| 2002/0122917 | A1 | 9/2002 | Halverson et al. |

FOREIGN PATENT DOCUMENTS

| | | |
|---|---|---|
| WO | WO-91/16425 | 10/1991 |
| WO | WO-97/16544 | 5/1997 |
| WO | WO-99/58716 | 11/1999 |
| WO | WO-00/40593 | 7/2000 |
| WO | WO-01/02452 | 1/2001 |
| WO | WO 01/66554 | 9/2001 |
| WO | WO-2004/050729 | 6/2004 |
| WO | WO-2004/093845 | 11/2004 |

OTHER PUBLICATIONS

Chevrier, Daniele et al., "Rapid detection of *Salmonella* subspecies I by PCR combined with non-radioactive hybridisation using covalently immobilised oligonucleotide on a microplate", *FEMS Immunology and Medical Microbiology*, vol. 10, No. 3-4 Feb. 1995, 245-251.

Collioud, Andre et al., "Oriented and Covalent Immobilization of Target Molecules to Solid Supports: Synthesis and Application of a Light-Activatable and Thiol-Reactive Cross-Linking Reagent", *Bioconjugate Chem*, vol. 4, No. 6 Nov./Dec. 1993, 528-536.

Kanazawa, Akihiko et al., "Polymeric Phosphonium Salts as a Novel Class of Cationic Biocides. VII. Synthesis and Antibacterial Activity of Polymeric Phosphonium Salts and Their Model Compounds Containing Long Alkyl Chains", *Journal of Applied Polymer Science*, vol. 53, No. 9 Aug. 29, 1994, 1237-1244.

Nagasawa, Junichi et al., "Immobilization of DNA via Covalent Linkage for Use as Immunosorbent", *Journal of Applied Biochemistry*, vol. 7 1985, 296-302.

Nagasawa, Junichi et al., "Immunosorbent Consisting of DNA Immobilized on Oxirane-Activated Sepharose", *Journal of Applied Biochemistry*, vol. 7 1985, 430-437.

"NucleoLink vs. Covalink Surfaces", *Nunc InterMed TechNote—Molecular Biology*, vol. 3, No. 17 Oct. 1995, 2 pages.

O'Donnell-Maloney, Maryanne J. et al., "The development of microfabricated arrays for DNA sequencing and analysis", *TIBTECH*, vol. 14 Oct. 1996, 401-407.

Pirri, Giovanna et al., "Characterization of a Polymeric Adsorbed Coating for DNA Microarray Glass Slides", *Anal. Chem.*, vol. 76 Mar. 1, 2004, 1352-1358.

"Reacti-Bind DNA Coating Solution", *PIERCE*, Pierce Chemical Company—Jan. 1997, 1 page.

Timofeev, Edward N. et al., "Regioselective immobilization of short oligonucleotides to acrylic copolymer gels", *Nucleic Acids Research* vol. 24, No. 16 1996, 3142-3148.

FIG. 1

ATTACHMENT OF MOLECULES TO SURFACES

CROSS REFERENCE TO RELATED APPLICATIONS

This application is a divisional of application Ser. No. 11/901,033, filed Sep. 14, 2007, now U.S. Pat. No. 7,829,317, issued Nov. 9, 2010 which is a divisional of application Ser. No. 10/677,022, filed Oct. 1, 2003, now U.S. Pat. No. 7,309,593, issued Dec. 18, 2007, which applications are incorporated herein by reference.

FIELD OF THE INVENTION

The present invention relates to methods, reagents, and substrates that can be used for, for example, immobilizing biomolecules, such as nucleic acids and proteins. In an embodiment, the present invention relates to surfaces coated with a polymer according to the present invention. In an embodiment, the present invention relates to methods for thermochemically and/or photochemically attaching molecules to a surface at a high density.

BACKGROUND

The immobilization of deoxyribonucleic acid (DNA) onto substrates has become an important aspect in the development of DNA-based assay systems as well as for other purposes, including the development of microfabricated arrays for DNA analysis. Substrates for immobilization include the surface of microwell plates, tubes, beads, microscope slides, silicon wafers or membranes.

Hybridization is the method used most routinely to measure biomolecules, e.g., nucleic acids, by base pairing to probes immobilized on a solid support. When combined with amplification techniques such as the polymerase chain reaction (PCR) or ligase chain reaction (LCR), hybridization assays are a powerful tool for diagnosis and research.

A desirable goal for current DNA microarrays is the ability to put an entire species genome on one chip. Also, the ability to place replicates of a smaller set of genes on one chip is desirable. Another sought after goal is that the chips give results that represent the actual population of a specific nucleic acid in a sample.

There is evidence that more hydrophobic surfaces, that are common in the industry, interfere with hybridization process near the surface (Hughes, et. al., *Nature Biotechnology* 19(4): p 342-347 April, 2001). Assignee's U.S. Pat. No. 6,465,178, demonstrated the utility of slides coated with polyacrylamide copolymers for bioassays in a microarray format. The hydrophilicity of the polyacrylamide backbone provides an environment where surface reactions mimic kinetics and thermodynamics of a solution phase (Dorris, et al., *BMC Biotechnology* Jun. 11, 2003). However, hydrophilic surfaces can increase spot size. Larger spot size limits the number of spots that can be placed in an array on a surface.

There remains a need for an improved surface that can provide a higher density of spots, and that can retain sufficient hydrophilic character in an aqueous environment and provide solution phase reaction kinetics on the surface.

SUMMARY

The present invention relates to methods, compositions, and substrates that can be used for, for example, immobilizing biomolecules, such as nucleic acids and proteins. The present invention can include or employ a polymer including a substantial amount of monomer or monomers including uncharged polar moieties other than primary amide, such as a polymer including an N-substituted acrylamide, N,N-disubstituted acrylamide, N-substituted methacrylamide, N,N-disubstituted methacrylamide, or mixture thereof.

In an embodiment, the present invention includes a substrate. The substrate includes a surface and a polymer. The polymer coats at least a portion of the surface. The polymer includes an effective amount of monomer comprising an uncharged polar moiety other than primary amide and of one or more pendant reactive groups configured to form a covalent bond with a biomolecule. In an embodiment, an effective amount is at least about 40 mol-% of the monomer in the polymer. In an embodiment, the polymer coating is effective to provide a contact angle of about 30° to about 60° for a sessile water drop.

In an embodiment, the present invention includes a substrate. The substrate includes a support surface and polymer coupled to the support surface. The polymer includes an effective amount of monomer comprising an uncharged polar moiety other than primary amide and of one or more reactive groups. In an embodiment, the polymer is configured to form covalent bonds with a biomolecule.

In an embodiment, the present invention includes a composition including polymer. The polymer includes an effective amount of monomer comprising an uncharged polar moiety other than primary amide and of one or more reactive groups configured to form covalent bonds with corresponding functional groups on a biomolecule. In an embodiment, the polymer can be configured to be covalently attached to a surface.

In an embodiment, the present invention includes a method of attaching a biomolecule to a surface of a substrate. The method can include providing a composition including polymer. The polymer can include an effective amount of monomer comprising an uncharged polar moiety other than primary amide and of one or more pendent reactive groups configured to form covalent bonds with corresponding functional groups on a biomolecule. The polymer can be configured to be covalently attached to the surface. The method can also include one or more of: coating and immobilizing the composition on the substrate surface; providing solution including biomolecule including one or more functional groups reactive with the reactive groups; applying an aliquot of the solution to the substrate surface; and forming covalent bonds between the reactive group and the functional group of the biomolecule.

In an embodiment, the present invention includes a microarray. The microarray can include a support surface, polymer covalently coupled to the support surface, and a biomolecule covalently bound to the polymer in discrete spots. The polymer can include an effective amount of monomer comprising an uncharged polar moiety other than primary amide and of one or more reactive groups.

3
DETAILED DESCRIPTION

Definitions

As used herein, the phrase "primary amide" refers to an amide moiety represented by the formula —$CONH_2$. A primary amide can also be referred to as an unsubstituted amide. It includes no substitutions on the amide nitrogen. It includes two hydrogen atoms bonded to the amide nitrogen.

As used herein, the term "about" modifying the quantity of an ingredient in the compositions of the invention or employed in the methods of the invention refers to variation in the numerical quantity that can occur, for example, through typical measuring and reagent handling procedures used for making polymer compositions, coated substrates, and microarrays in the real world; through inadvertent error in these procedures; through differences in the manufacture, source, or purity of the ingredients employed to make the compositions or carry out the methods; and the like. Whether or not modified by the term "about", the claims include equivalents to the quantities.

Polymers of the Present Invention

The present invention relates to methods, reagents, and substrates that can be used for, for example, immobilizing biomolecules, such as nucleic acids and proteins. The present methods, reagents, and substrates include a polymer including a substantial amount of monomer or monomers including uncharged polar moieties other than primary amide. In an embodiment, the present polymers can be employed on substrates that provide advantageously small spot size and/or advantageously large contact angle for materials spotted on the surface. Although not limiting to the present invention, it is believed that, in an embodiment, the present polymer can provide a higher density of spots while retaining a hydrophilic character in an aqueous environment to give solution phase reaction kinetics.

The present polymer can include a substantial amount of monomer or monomers including uncharged polar moieties other than primary amide. The uncharged polar moiety other than primary amide can be in the polymer backbone or a group pendant from the polymer backbone. In an embodiment, the polymer can be a copolymer including additional monomers. In an embodiment, the polymer can include one or more monomers with one or more reactive groups, e.g., thermochemically reactive, photochemically reactive, or like reactive groups.

An embodiment of a polymer including: a substantial amount of monomer or monomers including uncharged polar moieties other than primary amide; optional additional monomers (without uncharged polar moiety other than primary amide); and monomer with one or more reactive groups, e.g., thermochemically reactive, photochemically reactive, or like reactive groups can be represented, for example, by Formula A:

In Formula A: Each [ ] moiety represents a monomer present in the polymer, which can be present in any order, randomly, or as blocks. Each $R^s$ is independently H or $CH_3$. Each of a, b, c, d, e, and f is independently 1-6, 1-3, or 2 or 3.

Each X and Z is independently an uncharged polar moiety other than primary amide.

X can be, for example, —CO—NHR, —CO—$NR^1R^2$, —COOR, —OR, —S(O)(O)(R), —$R^1R^2$N—O, —$NR^1R^2$, —$R^1$CO(N—)$R^2$, —NCOOR, polyethylene glycol, or the like; in which each of R, $R^1$, or $R^2$ can independently be alkyl or substituted alkyl (e.g., lower alkyl or substituted lower alkyl), cyclic alkyl, substituted cyclic alkyl, heterocyclic alkyl, aryl, substituted aryl, heteroaryl, or the like. $R^1$ and $R^2$ can be joined to form a cyclic alkyl or aryl moiety. For example, each of R, $R^1$, or $R^2$ can independently be methyl, ethyl, isopropyl, t-butyl, octyl, —$CH_2OC_4H_9$, —$CH_2CH_2OH$, —$CH_2OH$, cyclopentyl, cyclohexyl, phenyl, benzyl, or the like. $NR^1R^2$ can be a cyclic amine, such as morpholine, an aromatic amine, such as pyridine, a lactam, such as caprolactam or pyrrolidone, or the like.

Z can be, for example, O, NH, NR, or the like.

Each Y is independently a group that is a primary amide or is not a polar uncharged moiety. Y can be, for example, alkyl, aryl, methylene, primary amide, or the like.

Each A is independently a reactive group (e.g., a thermochemically reactive group or a photoreactive group). Suitable reactive groups are described hereinbelow. One or more reactive groups can be employed, for example, to immobilize a molecule on a surface.

In Formula A, each of m, n, o, p, q, and r represents the mole fraction of the corresponding monomer in the polymer, and m+n represents a substantial mole fraction. For example, m+n can be about 40 to about 99 mol-%, about 40 to about 90 mol-%, about 40 to about 85 mol-%, about 60 to about 99 mol-%, about 60 to about 90 mol-%, about 60 to about 85 mol-%, about 75 to about 99 mol-%, about 75 to about 90 mol-%, about 75 to about 85 mol-%, about 85 to about 99 mol-%, or about 85 to about 90 mol-%. By way of further example, m+n can be about 40 mol-%, about 45 mol-%, about 50 mol-%, about 55 mol-%, about 60 mol-%, about 65 mol-%, about 70 mol-%, about 75 mol-%, about 80 mol-%, about 85 mol-%, about 90 mol-%, or about 95 mol-% monomer including an uncharged polar moiety other than primary amide. The present polymer can include any of these ranges or amounts not modified by about or any of these quantities individually.

One or more of o, p, or q can be zero.

In certain embodiments, r can be about 0.2 to about 30 mol-%, about 1 to about 25 mol-%, about 2.5 to about 25 mol-%, about 5 to about 20 mol-%, or about 5 to about 15 mol-%. The present polymer can include any of these ranges or amounts not modified by about or any of these quantities individually.

Suitable polymer backbones including uncharged polar moieties other than primary amide include polyethers (e.g., polyethylene glycol, polypropylene glycol), substituted polyalkyleneimines (e.g., substituted polyethyleneimine), and the like.

Suitable pendant uncharged polar moieties other than primary amide include, for example, substituted amide, ester, ether, sulfone, amine oxide, and the like. Suitable backbones for pendant uncharged polar moieties other than primary amide include alkyl, branched alkyl, polyether, and polyamine backbones, which can be formed from monomers such as vinyl monomers, acrylate ester monomers, secondary and tertiary acrylamide monomers, polyethylene glycol, polypropylene glycol, substituted polyethyleneimine, and the like.

In an embodiment, the present polymer includes a substantial amount of one or more monomers including an uncharged polar moiety other than primary amide such as: N-substituted acrylamide, N,N-disubstituted acrylamide, N-substituted methacrylamide, N,N-disubstituted methacrylamide, or mixture thereof; such as N,N-dimethylacrylamide, N,N-diethylacrylamide, N-isopropylacrylamide, N-t-butylacrylamide, N-octylacrylamide, N-cyclohexylacrylamide, N-phenylacrylamide, N-benzylacrylamide, N—(CH$_2$OC$_4$H$_9$)acrylamide, N—(CH$_2$CH$_2$OH)acrylamide, N—(CH$_2$OH)acrylamide, N—(CH$_2$CH$_2$CH$_2$OH)acrylamide, N-methylmethacrylamide, N-ethylmethacrylamide, N,N-dimethylmethacrylamide, N,N-diethylmethacrylamide, N-acryloylmorpholine, N-methacryloylmorpholine, N—(CH$_2$OC$_4$H$_9$)methacrylamide, N—(CH$_2$CH$_2$OH)methacrylamide, N—(CH$_2$OH) methacrylamide, mixtures thereof, or the like; hydroxyalkylacrylate (e.g., hydroxyethylacrylate), hydroxyalkylmethacrylate (e.g., hydroxyethylmethacrylate), alkyl or aryl acrylate, alkyl or aryl methacrylate, ethoxyethoxyethylacrylate, polypropyleneglycolmonomethacrylate, mixtures thereof, or the like; vinylpyrrolidone, vinylcaprolactam, N-vinyl-N-methylacetamide, vinylmethylether, 2-vinylpyridine-N-oxide, vinylmethylsulfone, mixtures thereof, or the like; ethyleneglycol, ethyleneimine, PEG derivative of monomethacrylate (e.g., PEG 200, 400, or 1000), mixtures thereof, or the like; any of various aminimides or mixtures thereof; mixtures thereof, or the like.

In an embodiment, the present polymer includes a substantial amount of one or more monomers including an uncharged polar moiety other than primary amide such as: N-substituted acrylamide, N,N-disubstituted acrylamide, N-substituted methacrylamide, N,N-disubstituted methacrylamide, or mixture thereof; such as N,N-dimethylacrylamide, N,N-diethylacrylamide, N-isopropylacrylamide, N-t-butylacrylamide, N-octylacrylamide, N-cyclohexylacrylamide, N-phenylacrylamide, N-benzylacrylamide, N—(CH$_2$OC$_4$H$_9$)acrylamide, N—(CH$_2$CH$_2$OH)acrylamide, N—(CH$_2$OH)acrylamide, N—(CH$_2$CH$_2$CH$_2$OH)acrylamide, N-methylmethacrylamide, N-ethylmethacrylamide, N,N-dimethylmethacrylamide, N,N-diethylmethacrylamide, N-acryloylmorpholine, N-methacryloylmorpholine, N—(CH$_2$OC$_4$H$_9$)methacrylamide, N—(CH$_2$CH$_2$OH)methacrylamide, N—(CH$_2$OH) methacrylamide, mixtures thereof, or the like; alkyl or aryl acrylate, alkyl or aryl methacrylate, ethoxyethoxyethylacrylate, polypropyleneglycolmonomethacrylate, mixtures thereof, or the like; vinylcaprolactam, N-vinyl-N-methylacetamide, vinylmethylether, 2-vinylpyridine-N-oxide, vinylmethylsulfone, mixtures thereof, or the like; ethyleneimine, PEG derivative of monomethacrylate (e.g., PEG 200, 400, or 1000), mixtures thereof, or the like; any of various aminimides or mixtures thereof; mixtures thereof, or the like.

In an embodiment, the present polymer includes poly-(2-ethyloxazolene) (i.e. acetylated polyethyleneimine), polyvinylpyrrolidone (PVP), polyvinylcaprolactam, PVP-co-vinylacetate, polypropyleneglycolmonomethacrylate, or the like.

In an embodiment, the present polymer includes a substantial amount of N-substituted acrylamide, N,N-disubstituted acrylamide, N-substituted methacrylamide, N,N-disubstituted methacrylamide, or mixture thereof. Such substituted acrylamide can include, for example, N,N-dimethylacrylamide, N,N-diethylacrylamide, N-isopropylacrylamide, N-t-butylacrylamide, N-octylacrylamide, N-cyclohexylacrylamide, N-phenylacrylamide, N-benzylacrylamide, N—(CH$_2$OC$_4$H$_9$)acrylamide, N—(CH$_2$CH$_2$OH)acrylamide, N—(CH$_2$OH)acrylamide, N—(CH$_2$CH$_2$CH$_2$OH)acrylamide, N-methylmethacrylamide, N-ethylmethacrylamide, N,N-dimethylmethacrylamide, N,N-diethylmethacrylamide, N-acryloylmorpholine, N-methacryloylmorpholine, N—(CH$_2$OC$_4$H$_9$)methacrylamide, N—(CH$_2$CH$_2$OH)methacrylamide, N—(CH$_2$OH)methacrylamide, mixtures thereof, or the like.

In an embodiment, the present polymer includes a substantial amount of N,N-dimethylacrylamide. In an embodiment, the present polymer includes poly(N,N-dimethylacrylamide). In an embodiment, the poly(N,N-dimethylacrylamide) is a copolymer including monomers with one or more thermochemically reactive groups, one or more photoreactive groups, or both. In an embodiment, the present dimethylacrylamide containing polymer can also include one or more thermochemically reactive groups, one or more photoreactive groups, or both. The thermochemically reactive group can be suitable, for example, for forming a covalent bond with a corresponding functional group of a biomolecule. The photoreactive group can be suitable, for example, for attaching the polymer to a surface. The present dimethylacrylamide containing polymer can be a copolymer.

The present polymer includes a substantial amount of monomer including an uncharged polar moiety other than primary amide. In an embodiment, the present polymer includes at least about 40 mol-% of the monomer including an uncharged polar moiety other than primary amide. For example, the present polymer can include monomer including an uncharged polar moiety other than primary amide at about 40 to about 99 mol-%, about 40 to about 90 mol-%, about 40 to about 85 mol-%, about 60 to about 99 mol-%, about 60 to about 90 mol-%, about 60 to about 85 mol-%, about 75 to about 99 mol-%, about 75 to about 90 mol-%, about 75 to about 85 mol-%, about 85 to about 99 mol-%, or about 85 to about 90 mol-%. By way of further example, the present polymer can include about 40 mol-%, about 45 mol-%, about 50 mol-%, about 55 mol-%, about 60 mol-%, about 65 mol-%, about 70 mol-%, about 75 mol-%, about 80 mol-%, about 85 mol-%, about 90 mol-%, or about 95 mol-% monomer including an uncharged polar moiety other than primary amide. The present polymer can include any of these ranges or amounts not modified by about or any of these quantities individually.

In an embodiment, the present polymer can be described by the contact angle formed by a drop on a surface coated with the polymer. The identity and mole fraction of the monomer or monomers including uncharged polar moieties other than primary amide in the present polymer can be selected to provide a particular or advantageous contact angle.

Contact angle represents a known way of describing fluids on surfaces. For example, contact angle can represent wetting characteristics, cleanliness, hydrophobicity, hydrophilicity, or like characteristics of a surface. Contact angle can be measured and calculated by any of a variety of known methods and apparatus. For example, contact angles have been measured for the present polymers with a Krüss DSA10 MK 2 goniometer (Krüss, Hamburg, Germany). From the measurement provided by a goniometer, contact angle can be calculated, for example, using the Fowkes method. This can be accomplished with a software package, such as that included with the Krüss goniometer. Measuring contact angle can employ, for example, a 3 µL sessile water drop touched to the surface and allowed to spread for 20 sec.

In an embodiment, the present polymer includes monomer or monomers including uncharged polar moieties other than primary amide of a type and in an amount effective to provide, when coated to form a surface, a surface with contact angle of about 30° to about 60° for a sessile water drop. In an embodiment the present polymer is effective to provide a contact angle of about 35° to about 55°, or of about 40° to about 50°. In general, these values of contact angle refer to contact angle on a clean polymer coated surface. In an embodiment, the present polymer includes a substantial amount of N,N-dimethylacrylamide.

In an embodiment, the present invention includes a hydrophilic copolymer composition that can confer a contact angle of between 30° to 60° to a sessile water drop on a surface coated with the polymer. The hydrophilic copolymer can be configured to be covalently attached to a surface. The hydrophilic copolymer can include one or more thermochemically reactive groups, which can be configured to form covalent bonds with corresponding functional groups on a biomolecule.

In an embodiment, the present polymer can be described by the spot size formed by a drop on a surface coated with the polymer. The identity and mole fraction of the monomer or monomers including uncharged polar moieties other than primary amide in the present polymer can be selected to provide advantageously small spot size.

A fluid can be spotted on a surface by any of a variety of methods to form, for example, an array or microarray of spots. Spots can be formed by known printing methods, such as contact printing or piezoelectric printing. Small spot size can allow more spots per unit area on the surface.

In an embodiment, the present polymer includes monomer or monomers including uncharged polar moieties other than primary amide of a type and in an amount effective to provide, when coated to form a surface, spot size of less than about 100 µm, about 20 to about 100 µm, or about 40 to about 80 µm. In an embodiment, the present polymer is effective to provide a surface with spot density of greater than about 2,500 spots per $cm^2$, or a spot density of greater than about 20,000 spots per $cm^2$. In an embodiment, the present polymer is effective to provide a surface with spot size only about 70% or even only about 60% the size of spots of the same reagent spotted on conventional more hydrophilic polymer surfaces. In an embodiment, the present polymer is effective to form smaller spots and to maintain increased or acceptable signal to noise ratio, compared to reagent spotted on conventional more hydrophilic polymer surfaces. For example, the present polymer can provide increased signal with the same background. In an embodiment, the present polymer includes a substantial amount of N,N-dimethylacrylamide.

In an embodiment, the present polymer can be described by its solubility in one or more organic solvents such as tetrahydrofuran (THF) or alcohol and, optionally, water. In an embodiment, the present polymer includes monomer or monomers including uncharged polar moieties other than primary amide of a type and in an amount effective to provide solubility in THF or alcohol (e.g., methanol, ethanol, or isopropanol) and, optionally, water. In an embodiment, the present polymer includes monomer or monomers including uncharged polar moieties other than primary amide of a type and in an amount effective to provide solubility in THF. In an embodiment, the present polymer is soluble in an alcohol, such as isopropanol, methanol, or ethanol, or the like. In contrast, conventional polyacrylamide based polymers are not particularly soluble in THF. Solubility can be determined by any of a variety of known methods, such as dissolving a particular amount of the polymer in a particular volume of solvent.

More About Polymers

The present polymer can be a synthetic polymer, such as a copolymer, resulting from, for example, addition, condensation, or free radical polymerization. A polymer according to the present invention can also include one or more monomers with one or more reactive groups, e.g., thermochemically reactive, photochemically reactive, like reactive groups, or mixtures thereof. Suitable additional monomers and reactive groups are described in U.S. Pat. Nos. 5,858,653 and 6,465,178 and in U.S. Published Patent Application 20030113792 (Ser. No. 09/521,545), the disclosures of which are incorporated herein by reference.

In an embodiment, the present polymers are capable of bearing the desired number and type of thermochemically reactive groups, and optionally photogroups, the combination dependent upon the reagent selected. The polymeric backbone can be selected to provide a spacer between the surface and the thermochemically reactive groups. In this manner, the reagent can be bonded to a surface or to an adjacent reagent molecule and can provide the other groups with sufficient freedom of movement to demonstrate suitable activity. In an embodiment, the polymer is biologically inert, e.g., it does not provide a biological function that is inconsistent with, or detrimental to, their use in the manner described.

Compositions of the invention can carry one or more pendent latent reactive groups covalently bound to the polymer backbone. Photoreactive groups are defined herein, and exemplary groups are sufficiently stable to be stored under conditions in which they retain such properties as described in U.S. Pat. No. 5,002,582, the disclosure of which is incorporated herein by reference. Latent reactive groups can be chosen that are responsive to various portions of the electromagnetic spectrum, with those responsive to ultraviolet and visible portions of the spectrum (referred to herein as "photoreactive") being typical.

Photoreactive groups respond to specific applied external stimuli to undergo active specie generation with resultant covalent bonding to an adjacent chemical structure, e.g., as provided by the same or a different molecule. Photoreactive groups are those groups of atoms in a molecule that retain their covalent bonds unchanged under conditions of storage but that, upon activation by an external energy source (e.g., light), form covalent bonds with other molecules. The photoreactive group can generate active species such as free radicals and particularly nitrenes, carbenes, and excited states of ketones upon absorption of electromagnetic energy. Photoreactive groups can be chosen to be responsive to various portions of the electromagnetic spectrum, and photoreactive groups that are responsive to e.g., ultraviolet and visible portions of the spectrum, are typical and may be referred to herein occasionally as "photochemical group" or "photogroup".

Photoreactive aryl ketones can be used, such as acetophenone, benzophenone, quinone, anthraquinone, anthrone, and anthrone-like heterocycles (i.e., heterocyclic analogs of anthrone such as those having N, O, or S in the 10-position), or their substituted (e.g., ring substituted) derivatives. In an embodiment, the functional groups of such ketones are used since they are readily capable of undergoing the activation/inactivation/reactivation cycle described herein. In one embodiment, benzophenone is used as a photoreactive moiety, since it is capable of photochemical excitation with the initial formation of an excited singlet state that undergoes intersystem crossing to the triplet state. The excited triplet state can insert into carbon-hydrogen bonds by abstraction of a hydrogen atom (from a substrate, for example), thus creating a radical pair. Subsequent collapse of the radical pair leads to formation of a new carbon-carbon bond. If a reactive bond (e.g., carbon-hydrogen) is not available for bonding, the ultraviolet light-induced excitation of the benzophenone group is reversible and the molecule returns to ground state energy level upon removal of the energy source. Photoactivatible aryl ketones such as benzophenone and acetophenone can be used inasmuch as these groups are subject to multiple reactivation in water and hence provide increased coating efficiency.

The azides constitute a class of photoreactive groups and include arylazides ($C_6R_5N_3$) such as phenyl azide and particularly 4-fluoro-3-nitrophenyl azide, acyl azides (—CO—$N_3$) such as benzoyl azide and p-methylbenzoyl azide, azido formates (—O—CO—N$_3$) such as ethyl azidoformate, phenyl azidoformate, sulfonyl azides (—SO$_2$—N$_3$) such as benzenesulfonyl azide, and phosphoryl azides (RO)$_2$PON$_3$ such as diphenyl phosphoryl azide and diethyl phosphoryl azide. Diazo compounds constitute another class of photoreactive groups and include diazoalkanes (—CHN$_2$) such as diazomethane and diphenyldiazomethane, diazoketones (—CO—CHN$_2$) such as diazoacetophenone and 1-trifluoromethyl-1-diazo-2-pentanone, diazoacetates (—O—CO—CHN$_2$) such as t-butyl diazoacetate and phenyl diazoacetate, and beta-keto-alpha-diazoacetates (—CO—CN$_2$—CO—O—) such as t-butyl alpha diazoacetoacetate. Other photoreactive groups include the diazirines (—CHN$_2$) such as 3-trifluoromethyl-3-phenyldiazirine, and ketenes (—CH=C=O) such as ketene and diphenylketene. In an embodiment, the photochemically reactive group includes acetophenone, benzophenone, quinone, anthraquinone, anthrone, heterocyclic analog of anthrone, or mixtures thereof. In an embodiment, the photochemically reactive group includes a photoreactive aryl ketone.

Upon activation of the photoreactive groups, the polymer composition is covalently bound to the material surface by covalent bonds through residues of the photoreactive groups. Exemplary photoreactive groups, and their residues upon activation, are listed in Table A.

TABLE A

| Photoreactive | Group | Residue Functionality |
|---|---|---|
| aryl azides | amine | R—NH—R' |
| acyl azides | amide | R—CO—NH—R' |
| azidoformates | carbamate | R—O—CO—NH—R' |
| sulfonyl azides | sulfonamide | R—SO$_2$—NH—R' |
| phosphoryl azides | phosphoramide | (RO)$_2$PO—NH—R' |
| diazoalkanes | new C—C bond | |
| diazoketones | new C—C bond and ketone | |
| diazoacetates | new C—C bond and ester | |
| beta-keto-alpha-diazoacetates | new C—C bond and beta-ketoester | |
| aliphatic azo | new C—C bond | |
| diazirines | new C—C bond | |
| ketenes | new C—C bond | |
| photoactivated ketones | new C—C bond and alcohol | |

Any of a variety of known thermochemically reactive groups are suitable to provide covalent immobilization of a biomolecule, such as an appropriately derivatized nucleic acid. For example, an amino derivatized nucleic acid sequence can undergo a covalent coupling reaction with an activated ester such as an N-oxysuccinimide (NOS) ester to provide an amide linking group. Similar activated esters such as p-nitrophenyl and pentafluorophenyl esters can also provide amide links when reacted with amine groups. The present invention can also employ any of numerous other amine-reactive functional groups such as isocyanates, thioisocyanates, carboxylic acid chlorides, epoxides, aldehydes, alkyl halides and sulfonate esters, such as mesylate, tosylate and tresylate, each of which could serve as the thermochemically reactive group. Suitable thermochemically reactive groups include esters (e.g., NOS), epoxide, azlactone, activated hydroxyl, and maleimide groups. In an embodiment, the thermochemically reactive group includes NOS, epoxide, aldehyde, isothiocyanate, or mixtures thereof.

In an embodiment, the biomolecule (e.g., nucleic acid) can be derivatized with a sulfhydryl group using techniques well known in the art. The corresponding thermochemically reactive group can be, for example, a maleimide ring structure or an α-iodoacetamide. Either of these structures can react readily to provide a covalent linkage with the sulfhydryl derivatized nucleic acid sequence.

In another embodiment the polymer composition can contain epoxide groups, such as glycidyl methacrylate, as the thermochemically reactive group. In this embodiment, a biomolecule (e.g., DNA) is not required to be derivatized with a corresponding functional group.

The functionalized polymers of this invention can be prepared by appropriate derivatization of a preformed polymer or by polymerization of a set of comonomers to give the desired substitution pattern. The latter approach allows easily changing the ratio of the various comonomers and the ability to control the level of incorporation into the polymer. A combination of these two approaches can also be used to provide advantageous structures.

In an embodiment, for instance, monomers can be prepared having a polymerizable group at one end of the molecule, separated by a spacer group from a photoreactive or thermochemically reactive group at the other end. For example, polymerizable vinyl groups such as acrylamides, acrylates, or maleimides can be coupled through a short hydrocarbon spacer to an activated ester such as a NOS ester or to a photoreactive group such as a substituted benzophenone. These compounds can be prepared and purified using known techniques of organic synthesis.

Polymers and copolymers can be prepared from the above monomers as well, using known techniques. For example, these monomers and comonomers undergo free radical polymerization using known azo initiators such as azobis(2-methyl-butyronitrile) (Vazo-67) or redox reagents for initiation using known redox reagents, such as N,N-diethylaniline and benzoyl peroxide or the like, to make the desired copolymers. Other free radical generation methods are known and can be used. The monomers selected for the polymerization are chosen based on the nature of the final polymer product. For example, a photoreactive polymer containing a NOS group can be prepared from a monomer containing the photoreactive group and a second monomer containing the activated NOS ester.

The composition of the final polymer can be controlled by the mole ratio of the monomers charged to the polymerization reaction. Typically monomers including reactive groups are used at a lower mole percentage of total monomers than the monomer including an uncharged polar moiety other than primary amide. Based on the relative reactivities of the monomers used, the distribution of the monomers along the backbone can be largely random.

The present polymer can include one or more thermochemically reactive groups, one or more photoreactive groups, or a mixture thereof. In certain embodiments, the present polymer includes a thermochemically reactive group and/or a photoreactive group at about 0.2 to about 30 mol-%, about 1 to about 25 mol-%, about 2.5 to about 25 mol-%, about 5 to about 20 mol-%, or about 5 to about 15 mol-%. The present polymer can include any of these ranges or amounts not modified by about or any of these quantities individually.

Polymer Coated Surfaces

In an embodiment, the present invention can provide a surface suitable for immobilizing a biomolecule, such as a nucleic acid. Immobilizing a biomolecule can employ a reactive group, such as a thermochemically reactive group of the polymer. For example, the surface of the material to be coated can include one or more thermochemically reactive groups, which can be used to immobilize an embodiment of the present polymer including one or more thermochemically reactive groups. Suitable thermochemically reactive groups include activated esters (e.g., NOS), epoxide, azlactone, activated hydroxyl, and maleimide groups.

The surface can be treated to accept polymer groups by any of a variety of known methods. For example, the surface can be treated with an ammonia plasma to introduce reactive amines onto the surface. In an embodiment, the amine surface can be treated with an embodiment of the present polymer including, for example, thermochemically reactive groups (e.g., NOS groups). The polymer can be immobilized through reaction of the NOS groups with corresponding amine groups on the surface. The reactive groups on the polymer can be in excess relative to the reactive groups on the surface. Such excess can insure that a sufficient number of the polymer thermochemically reactive groups remain following immobilization to allow coupling to a biomolecule.

In an embodiment, immobilizing a biomolecule on a surface can employ a reactive group, such as a thermochemically reactive group of the polymer. For example, the surface of the material to be coated can include one or more groups that can react with the photochemically reactive group on the polymer. Suitable photochemical groups are described hereinabove.

The present polymer composition can be immobilized on the surface of a slide. The slide can be stably stored and used at a later date to prepare microarrays. In an embodiment, coupling of a biomolecule to the surface can take place at pH 7-9 in a humid environment following printing the DNA solution in the form of small spots.

Slides or activated slides of the present invention are particularly well suited to replace conventional (e.g., silylated) glass slides in the preparation of microarrays using known manufacturing or processing protocols, reagents, or equipment. Suitable commercially available equipment and protocols include micro-spotting robots (e.g., as available from Apogent Discoveries, Hudson, N.H.), chipmaker micro-spotting devices (e.g., as available from TeleChem International, Sunnyvale, Calif.).

The methods and compositions of the present invention can provide a substrate, such as a glass slide (e.g., an activated glass slide). Such a slide can be configured for including or fabricating a microarray. The substrate can have a surface including one or more microarrays. Each microarray can include at least about $100/cm^2$ (and preferably at least about $2,500/cm^2$) distinct bound biomolecules (e.g., polynucleotides or polypeptides). Each distinct bound biomolecule can be disposed at a separate, defined position in the array and can be deposited in a volume, for example, in the range of about 0.01 nL to about 100 nL. For example, the slide can be configured to receive sample in an amount of twenty nanoliters or less.

The regions (e.g., discrete spots) within the array can be generally circular in shape and can be separated from one another, for example, by about their largest diameter. A plurality of bound biomolecules can be provided, such that each region includes a single, and preferably different, bound biomolecule. In an embodiment, the spots are generally circular in shape, have a diameter of about 20 microns to about 100 microns, and are separated from other spots in the array by center to center spacing of about 40 microns to about 120 microns.

In an embodiment, the biomolecule includes a nucleic acid. The nucleic acid can be immobilized on the surface of a substrate such as plastic, silicon hydride, or organosilane-pretreated glass or silicon slide.

The present polymers can be employed for immobilizing any of a variety of biomolecules. The biomolecule can be unmodified or modified with a functional group to aid in immobilization. Suitable biomolecules include modified or unmodified oligo and polynucleotides (e.g., DNA or RNA), such as plasmid DNA, cosmid DNA, bacteriophage DNA, genomic DNA (including yeast, viral, bacterial, mammalian, insect, or like genomic DNA), cDNA, peptide nucleic acid, protein, carbohydrate, peptide, cell, tissue, and the like. In an embodiment, the biomolecule includes polypeptide or nucleic acid.

The biomolecule can optionally be functionalized or modified by any of a variety of known methods. For example, during synthesis, biomolecules, such as oligonucleotides or nucleic acids, can be prepared with functional groups such as amines or sulfhydryl groups in order to be reactive to NOS groups in the polymer composition. In an embodiment, the biomolecule includes a nucleic acid that includes an amine group, a sulfhydryl group, or a mixture thereof.

The present invention provides a method and polymer composition for covalent attachment of bio- or other molecules onto the surface of a substrate, such as slides formed of organosilane-pretreated glass, organosilane-pretreated silicon, silicon hydride, or plastic. Silane treatment of the substrate surface, before the polymer composition is applied, can follow any of the procedures well known in the art. In an embodiment, the method and polymer composition can immobilize nucleic acid probes onto plastic materials such as microwell plates, e.g., for use in hybridization assays. In an embodiment, the method and polymer composition are adapted for use with substantially flat or molded surfaces, such as those provided by organosilane-pretreated glass, organosilane-pretreated silicon, silicon hydride, or plastic (e.g., polymethylmethacrylate, polystyrene, polycarbonate, polyethylene, or polypropylene). The polymer composition can then be used to covalently attach a probe molecule such as a biomolecule (e.g., a nucleic acid) which in turn can be used for specific binding reactions (e.g., to hybridize a nucleic acid to a biomolecule).

Substrates (e.g., slides, microspheres, microbeads, and polymer membranes) can be prepared from a variety of materials, including but not limited to plastic materials selected from the group consisting of crystalline thermoplastics (e.g., high and low density polyethylenes, polypropylenes, acetal resins, nylons, and thermoplastic polyesters) and amorphous thermoplastics (e.g., polycarbonates, polystyrene, and poly (methyl methacrylates) and glass. In an embodiment, suitable plastic or glass materials can provide a desired combination of such properties as rigidity, surface uniformity, resistance to long term deformation, and resistance to thermal degradation.

The present invention includes methods of making and using polymer compositions, substrates coated with the polymer compositions, and microarrays on the coated substrates. Methods of making the polymer compositions can include any of a variety of conventional polymer synthesis procedures. The present methods typically employ the monomer including uncharged polar moiety other than primary amide and a monomer including a reactive group. Specific embodiments of methods of making certain of the present polymer compositions are detailed in the examples.

Coating the present polymer compositions on a substrate can employ any of a variety of known coating techniques. During or after coating, the polymer composition can be immobilized on the substrate. For example, using a thermochemically reactive group, the present polymer composition can be immobilized on the substrate by heating. For example, using a photochemically reactive group, the present polymer composition can be immobilized on the substrate by exposing to electromagnetic radiation, such as light. Methods for immobilizing polymers on substrates with thermochemically or photochemically reactive groups are known.

The polymer coated substrate can be treated with biomolecule. The biomolecule can be immobilized in a spot on the substrate, for example, using thermochemically or photochemically reactive groups and using modified or unmodified biomolecule. Immobilizing typically includes covalent bonding between the reactive group and one or more functional groups on the biomolecule.

The present invention may be better understood with reference to the following examples. These examples are intended to be representative of specific embodiments of the invention, and are not intended as limiting the scope of the invention.

EXAMPLES

Unless otherwise indicated, all percentages are by weight. Structures of the various "Compounds" identified throughout these Examples can be found in Table 1 included below. NMR analyses were run on an 80 Mhz spectrometer unless otherwise stated.

Table 1 Compounds

Compound I (BBA)

Compound II (APMA-HCL)

Compound III (BBA-APMA)

Compound IV (MAL-EAC-NOS)

15

Compound V (Photo-DMA-NOS)

Compound VI (APMA-NCS)

Compound VII (DMA-APMA)

Comparative Compound VIII

16

Comparative Compound IX

Compound X

Compound XI

Comparative Compound XII

Compound XIII

Compound XIV

Example 1

Preparation of 4-Benzoylbenzoyl Chloride (BBA-Cl) (Compound I)

4-Benzoylbenzoic acid (BBA), 1.0 kg (4.42 moles), was added to a dry 5 liter Morton flask equipped with reflux condenser and overhead stirrer, followed by the addition of 645 ml (8.84 moles) of thionyl chloride and 725 ml of toluene. Dimethylformamide, 3.5 ml, was then added and the mixture was heated at reflux for 4 hours. After cooling, the solvents were removed under reduced pressure and the residual thionyl chloride was removed by three evaporations using 3×500 ml of toluene. The product was recrystallized from 1:4 toluene:hexane to give 988 g (91% yield) after drying in a vacuum oven. Product melting point was 92-94° C. Nuclear magnetic resonance (NMR) analysis ($^1$H NMR (CDCl$_3$)) was consistent with the desired product: aromatic protons 7.20-8.25 (m, 9H). All chemical shift values are in ppm downfield from a tetramethylsilane internal standard. The final compound was stored for use in the preparation of a monomer used in the synthesis of Compound III.

Example 2

Preparation of N-(3-Aminopropyl)methacrylamide Hydrochloride (APMA-HCL) (Compound II)

A solution of 1,3-diaminopropane, 1910 g (25.77 moles), in 1000 ml of $CH_2Cl_2$ was added to a 12 liter Morton flask and cooled on an ice bath. A solution of t-butyl phenyl carbonate, 1000 g (5.15 moles), in 250 ml of $CH_2Cl_2$ was then added dropwise at a rate which kept the reaction temperature below 15° C. Following the addition, the mixture was warmed to room temperature and stirred for 2 hours. The reaction mixture was diluted with 900 ml of $CH_2Cl_2$ and 500 g of ice, followed by the slow addition of 2500 ml of 2.2 N NaOH. After testing to insure the solution was basic, the product was transferred to a separatory funnel and the organic layer was removed and set aside as extract #1. The aqueous portion was then extracted with 3×1250 ml of $CH_2Cl_2$, keeping each extraction as a separate fraction. The four organic extracts were then washed successively with a single 1250 ml portion of 0.6 N NaOH beginning with fraction #1 and proceeding through fraction #4. This wash procedure was repeated a second time with a fresh 1250 ml portion of 0.6 N NaOH. The organic extracts were then combined and dried over $Na_2SO_4$. Filtration and evaporation of solvent to a constant weight gave 825 g of N-mono-t-BOC-1,3-diaminopropane which was used without further purification.

A solution of methacrylic anhydride, 806 g (5.23 moles), in 1020 ml of $CHCl_3$ was placed in a 12 liter Morton flask equipped with overhead stirrer and cooled on an ice bath. Phenothiazine, 60 mg, was added as an inhibitor, followed by the dropwise addition of N-mono-t-BOC-1,3-diaminopropane, 825 g (4.73 moles), in 825 ml of $CHCl_3$. The rate of addition was controlled to keep the reaction temperature below 10° C. at all times. After the addition was complete, the ice bath was removed and the mixture was left to stir overnight. The product was diluted with 2400 ml of water and transferred to a separatory funnel. After thorough mixing, the aqueous layer was removed and the organic layer was washed with 2400 ml of 2 N NaOH, insuring that the aqueous layer was basic. The organic layer was then dried over $Na_2SO_4$ and filtered to remove drying agent. A portion of the $CHCl_3$ solvent was removed under reduced pressure until the combined weight of the product and solvent was approximately 3000 g. The desired product was then precipitated by slow addition of 11.0 liters of hexane to the stirred $CHCl_3$ solution, followed by overnight storage at 4° C. The product was isolated by filtration and the solid was rinsed twice with a solvent combination of 900 ml of hexane and 150 ml of $CHCl_3$. Thorough drying of the solid gave 900 g of N-[3-(N-tert-butyloxycarbonylamino)-propyl]-methacrylamide, m.p. 85.8° C. by DSC (Differential Scanning Calorimeter). Analysis on an NMR spectrometer was consistent with the desired product: $^1H$ NMR ($CDCl_3$) amide NH's 6.30-6.80, 4.55-5.10 (m, 2H), vinyl protons 5.65, 5.20 (m, 2H), methylenes adjacent to N 2.90-3.45 (m, 4H), methyl 1.95 (m, 3H), remaining methylene 1.50-1.90 (m, 2H), and t-butyl 1.40 (s, 9H).

A 3-neck, 2 liter round bottom flask was equipped with an overhead stirrer and gas sparge tube. Methanol, 700 ml, was added to the flask and cooled on an ice bath. While stirring, HCl gas was bubbled into the solvent at a rate of approximately 5 liters/minute for a total of 40 minutes. The molarity of the final HCl/MeOH solution was determined to be 8.5 M by titration with 1 N NaOH using phenolphthalein as an indicator. The N-[3-(N-tert-butyloxycarbonylamino)-propyl]-methacrylamide, 900 g (3.71 moles), was added to a 5 liter Morton flask equipped with an overhead stirrer and gas outlet adapter, followed by the addition of 1150 ml of methanol solvent. Some solids remained in the flask with this solvent volume. Phenothiazine, 30 mg, was added as an inhibitor, followed by the addition of 655 ml (5.57 moles) of the 8.5 M HCl/MeOH solution. The solids slowly dissolved with the evolution of gas but the reaction was not exothermic. The mixture was stirred overnight at room temperature to insure complete reaction. Any solids were then removed by filtration and an additional 30 mg of phenothiazine were added. The solvent was then stripped under reduced pressure and the resulting solid residue was azeotroped with 3×1000 ml of isopropanol with evaporation under reduced pressure. Finally, the product was dissolved in 2000 ml of refluxing isopropanol and 4000 ml of ethyl acetate were added slowly with stirring. The mixture was allowed to cool slowly and was stored at 4° C. overnight. Compound II was isolated by filtration and was dried to constant weight, giving a yield of 630 g with a melting point of 124.7° C. by DSC. Analysis on an NMR spectrometer was consistent with the desired product: $^1H$ NMR ($D_2O$) vinyl protons 5.60, 5.30 (m, 2H), methylene adjacent to amide N 3.30 (t, 2H), methylene adjacent to amine N 2.95 (t, 2H), methyl 1.90 (m, 3H), and remaining methylene 1.65-2.10 (m, 2H). The final compound was stored for use in the preparation of Compound III.

Example 3

Preparation of N-[3-(4-Benzoylbenzamido)propyl]methacrylamide (BBA-APMA) (Compound III)

Compound II 120 g (0.672 moles), prepared according to the general method described in Example 2, was added to a dry 2 liter, three-neck round bottom flask equipped with an overhead stirrer. Phenothiazine, 23-25 mg, was added as an inhibitor, followed by 800 ml of chloroform. The suspension was cooled below 10° C. on an ice bath and 172.5 g (0.705 moles) of Compound I, prepared according to the general method described in Example 1, were added as a solid. Triethylamine, 207 ml (1.485 moles), in 50 ml of chloroform was then added dropwise over a 1-1.5 hour time period. The ice bath was removed and stirring at ambient temperature was continued for 2.5 hours. The product was then washed with 600 ml of 0.3 N HCl and 2×300 ml of 0.07 N HCl. After drying over sodium sulfate, the chloroform was removed under reduced pressure and the product was recrystallized twice from 4:1 toluene:chloroform using 23-25 mg of phenothiazine in each recrystallization to prevent polymerization. Typical yields of Compound III were 90% with a melting point of 147-151° C. Analysis on an NMR spectrometer was consistent with the desired product: $^1H$ NMR ($CDCl_3$) aromatic protons 7.20-7.95 (m, 9H), amide NH 6.55 (broad t, 1H), vinyl protons 5.65, 5.25 (m, 2H), methylene adjacent to amide N's 3.20-3.60 (m, 4H), methyl 1.95 (s, 3H), and remaining methylene 1.50-2.00 (m, 2H). The final compound was stored for use in the synthesis of photoactivatable polymers as described, for instance, in Examples 5 and 6.

Example 4

Preparation of N-Succinimidyl 6-Maleimidohexanoate (MAL-EAC-NOS) (Compound Iv)

A functionalized monomer was prepared in the following manner, and was used as described in Examples 5 and 6 to introduce activated ester groups on the backbone of a polymer. 6-Aminohexanoic acid, 100 g (0.762 moles), was dissolved in 300 ml of acetic acid in a three-neck, 3 liter flask equipped with an overhead stirrer and drying tube. Maleic anhydride, 78.5 g (0.801 moles), was dissolved in 200 ml of acetic acid and added to the 6-aminohexanoic acid solution. The mixture was stirred one hour while heating on a boiling water bath, resulting in the formation of a white solid. After cooling overnight at room temperature, the solid was collected by filtration and rinsed with 2×50 ml of hexane. After drying, the typical yield of the (Z)-4-oxo-5-azaundec-2-enedioic acid was 158-165 g (90-95%) with a melting point of 160-165° C. Analysis on an NMR spectrometer was consistent with the desired product: $^1$H NMR (DMSO-$d_6$) amide proton 8.65-9.05 (m, 1H), vinyl protons 6.10, 6.30 (d, 2H), methylene adjacent to nitrogen 2.85-3.25 (m, 2H), methylene adjacent to carbonyl 2.15 (t, 2H), and remaining methylenes 1.00-1.75 (m, 6H).

(Z)-4-oxo-5-azaundec-2-enedioic acid, 150.0 g (0.654 moles), acetic anhydride, 68 ml (73.5 g, 0.721 moles), and phenothiazine, 500 mg, were added to a 2 liter three-neck round bottom flask equipped with an overhead stirrer. Triethylamine, 91 ml (0.653 moles), and 600 ml of THF were added and the mixture was heated to reflux while stirring. After a total of 4 hours of reflux, the dark mixture was cooled to about 60° C. and poured into a solution of 250 ml of 12 N HCl in 3 liters of water. The mixture was stirred 3 hours at room temperature and then was filtered through a filtration pad (Celite 545, J. T. Baker, Jackson, Tenn.) to remove solids. The filtrate was extracted with 4×500 ml of chloroform and the combined extracts were dried over sodium sulfate. After adding 15 mg of phenothiazine to prevent polymerization, the solvent was removed under reduced pressure. The 6-maleimidohexanoic acid was recrystallized from 2:1 hexane:chloroform to give typical yields of 76-83 g (55-60%) with a melting point of 81-85° C. Analysis on a NMR spectrometer was consistent with the desired product: $^1$H NMR (CDCl$_3$) maleimide protons 6.55 (s, 2H), methylene adjacent to nitrogen 3.40 (t, 2H), methylene adjacent to carbonyl 2.30 (t, 2H), and remaining methylenes 1.05-1.85 (m, 6H).

The 6-maleimidohexanoic acid, 20.0 g (94.7 mmol), was dissolved in 100 ml of chloroform under an argon atmosphere, followed by the addition of 41 ml (0.47 mol) of oxalyl chloride. After stirring for 2 hours at room temperature, the solvent was removed under reduced pressure with 4×25 ml of additional chloroform used to remove the last of the excess oxalyl chloride. The acid chloride was dissolved in 100 ml of chloroform, followed by the addition of 12 g (0.104 mol) of N-hydroxysuccinimide and 16 ml (0.114 mol) of triethylamine. After stirring overnight at room temperature, the product was washed with 4×100 ml of water and dried over sodium sulfate. Removal of solvent gave 24 g of product (82%) which was used without further purification. Analysis on an NMR spectrometer was consistent with the desired product: $^1$H NMR (CDCl$_3$) maleimide protons 6.60 (s, 2H), methylene adjacent to nitrogen 3.45 (t, 2H), succinimidyl protons 2.80 (s, 4H), methylene adjacent to carbonyl 2.55 (t, 2H), and remaining methylenes 1.15-2.00 (m, 6H). The final compound was stored for use in the synthesis of photoactivatable polymers as described, for instance, in Examples 5 and 6.

Example 5

Preparation of Copolymer of N,N-dimethylacrylamide (DMA), BBA-APMA, and MAL-EAC-NOS (Photo DMA-NOS) (Compound $V_A$)(Azo)

A photoactivatable copolymer was prepared in the following manner. DMA, 41.46 g (419 mmol), Compound III, prepared according to the general method described in Example 3, 1.56 g (4.5 mmol), Compound IV, prepared according to the general method described in Example 4, 6.88 g (22.3 mmol), and azobis(2-methyl-butyronitrile) (Vazo-67) 1.4 g (7.3 mmol) were dissolved in 200 ml of tetrahydrofuran (THF). The THF solution was added to a second stirred refluxing solution of Vazo 67 0.34 g (1.8 mmol) in THF (50 ml) under an inert atmosphere over one hour. The solution was refluxed overnight with stirring under an inert atmosphere. The polymer was isolated by slow addition of the THF solution to vigorously stirred hexanes (2500 ml). The precipitated polymer product was isolated by filtration and the filter cake was rinsed thoroughly with 200 ml hexanes. The product was dried under vacuum at 30° C. to give 51.7 g of a white solid.

The above procedure was also used to prepare compounds $V_B$—$V_I$, as shown below in Table 2 to provide between 50 and 52 g of polymer products.

TABLE 2

| Example | DMA Wt (g) | DMA Mole % | Compound III Wt (g) | Compound III Mole % | Compound IV Wt (g) | Compound IV Mole % | Vazo 67 Wt) (g) |
|---|---|---|---|---|---|---|---|
| $V_A$ | 41.56 | 94.00 | 1.56 | 1.00 | 6.88 | 5.00 | 1.70 |
| $V_B$ | 38.65 | 91.50 | 1.49 | 1.00 | 9.86 | 7.50 | 1.60 |
| $V_C$ | 35.99 | 89.00 | 1.43 | 1.00 | 12.58 | 10.00 | 1.60 |
| $V_D$ | 40.88 | 93.50 | 2.32 | 1.50 | 6.80 | 5.00 | 1.70 |
| $V_E$ | 38.03 | 91.00 | 2.22 | 1.50 | 9.75 | 7.50 | 1.60 |
| $V_F$ | 35.42 | 88.50 | 2.12 | 1.50 | 12.45 | 10.00 | 1.50 |
| $V_G$ | 40.22 | 93.00 | 3.06 | 2.00 | 6.73 | 5.00 | 1.70 |
| $V_H$ | 37.43 | 90.50 | 2.92 | 2.00 | 9.65 | 7.50 | 1.60 |
| $V_I$ | 34.87 | 88.00 | 2.80 | 2.00 | 12.33 | 10.00 | 1.50 |

Example 6

Preparation of Copolymer of N,N-dimethylacrylamide (DMA), BBA-APMA, and MAL-EAC-NOS (Photo DMA-NOS) (Compound V)(Redox)

A photoactivatible copolymer was prepared in the following manner. DMA 38.65 g (390 mmole); Compound III, prepared according to the general method described in Example 3, 1.5 g (4.3 mmol); Compound IV, prepared according to the general method described in Example 4, 9.9 g (32.1 mmol); and benzoyl peroxide 3.1 g (13.0 mmol) were dissolved in THF (200 ml). The THF solution was added to a second stirred solution of THF (50 ml) containing 1.9 g (13.0 mmol) N,N-diethylaniline under an inert atmosphere at room temperature over one hour. The solution was stirred overnight at room temperature under an inert atmosphere. The polymer was isolated by slow addition of the THF solution to vigorously stirred hexanes (2500 ml). The precipitated polymer product was isolated by filtration and the filter cake was rinsed thoroughly with 200 ml hexanes. The product was dried under vacuum at 30° C. to give 43 g of a gray solid.

Example 7

Production of Slides Coated with the Polymer (Photo DMA-NOS)(Compound V)

Soda lime microscope glass slides (Erie Scientific, Portsmouth, N.H.) were silane treated by dipping in a mixture of N-decyldimethylchlorosilane and p-tolyldimethylchlorosilane (United Chemical Technologies, Bristol, Pa.), 1% each in acetone, for one minute. After air drying, the slides were cured in an oven at 110° C. for a minimum of 30 minutes. Slides were then washed with acetone followed by dipping in deionized (DI) water. Finally, the slides were further dried in an oven for 10 minutes at 110° C.

Silane treated slides were then coated with a polymer composition by a variation of known methods. For example Compound V (Table 2) at 2 mg/ml, was sprayed onto the silane treated slides, which was then illuminated using a Dymax Lamp (25 mjoule/cm$^2$ as measured at 335 nm with a 10 nm band pass filter on an International Light radiometer) while wet, washed with deionized water, and dried. Oligonucleotides were printed on these slides using MicroGrid II arrayer (Apogent Discoveries, Hudson, N.H.). Two oligo nucleotides were immobilized on the coated slides. Sequence of Oligo 1 was, GCC ATG TGC AGT CTG GTT CAG GTT CAT AAA (SEQ ID NO:1) and was labeled with TAMRA (carboxytetramethylrhodamine, Integrated DNA Technologies, Inc., Coralville, Iowa) dye on 3' end and C6 amino linker on the 5' end. Oligo 2 was the same sequence as Oligo 1 except that it was terminated with Biotin on the 3' end. Both the oligos were printed at 10 µM concentration in 50 mM sodium phosphate buffer and 0.001% sodium dodecyl sulfate. Immediately after printing, slides were placed overnight in a sealed sodium chloride chamber to maintain 75% relative humidity. The printed slides were then washed with a pre-warmed solution of 50 mM ethanolamine in 0.1 M Tris, pH 9.0 (Sigma, St. Louis, Mo.) at 45° C. for 30 minutes followed by another wash in pre-warmed 0.1% N-lauryl sarcosine (Sigma, St. Louis, Mo.) in 5×SSC (75 mM sodium citrate, 0.75 M sodium chloride) for 1.5 hours at 45° C. Finally the slides were soaked in 10 mM citrate buffer at room temperature for 15 minutes and centrifuged to dry. Slides with Oligo 1 were scanned on GenePix 4000B microarray scanner (Axon Instruments, Union City, Calif.). Slides with Oligo 2 were developed in a 1:500 solution of Streptavidin-Cy5 (Amersham Biosciences, Piscataway, N.J.) prepared in TNB (10 mM Tris pH 8, 150 mM sodium chloride, 5% w/v blocking reagent) at room temperature for 30 minutes. Subsequently the slides were washed 3 times in TNT (10 mM Tris pH 8, 150 mM sodium chloride, 0.05% v/v Tween 20), 5 minutes each time followed by similar number of washes in deionized water. The slides were dried in a centrifuge and scanned on GenePix 4000B scanner.

In addition, contact angle of the spot on the substrate was measured. Contact angle data on a 3 µL sessile DI water drop was touched to the surface and allowed to spread for 20 seconds. Contact angle data was collected on a Krüiss DSA MK2 goniometer (Krüss, Hamburg, Germany) and calculated using the Fowkes method.

Figure 1:
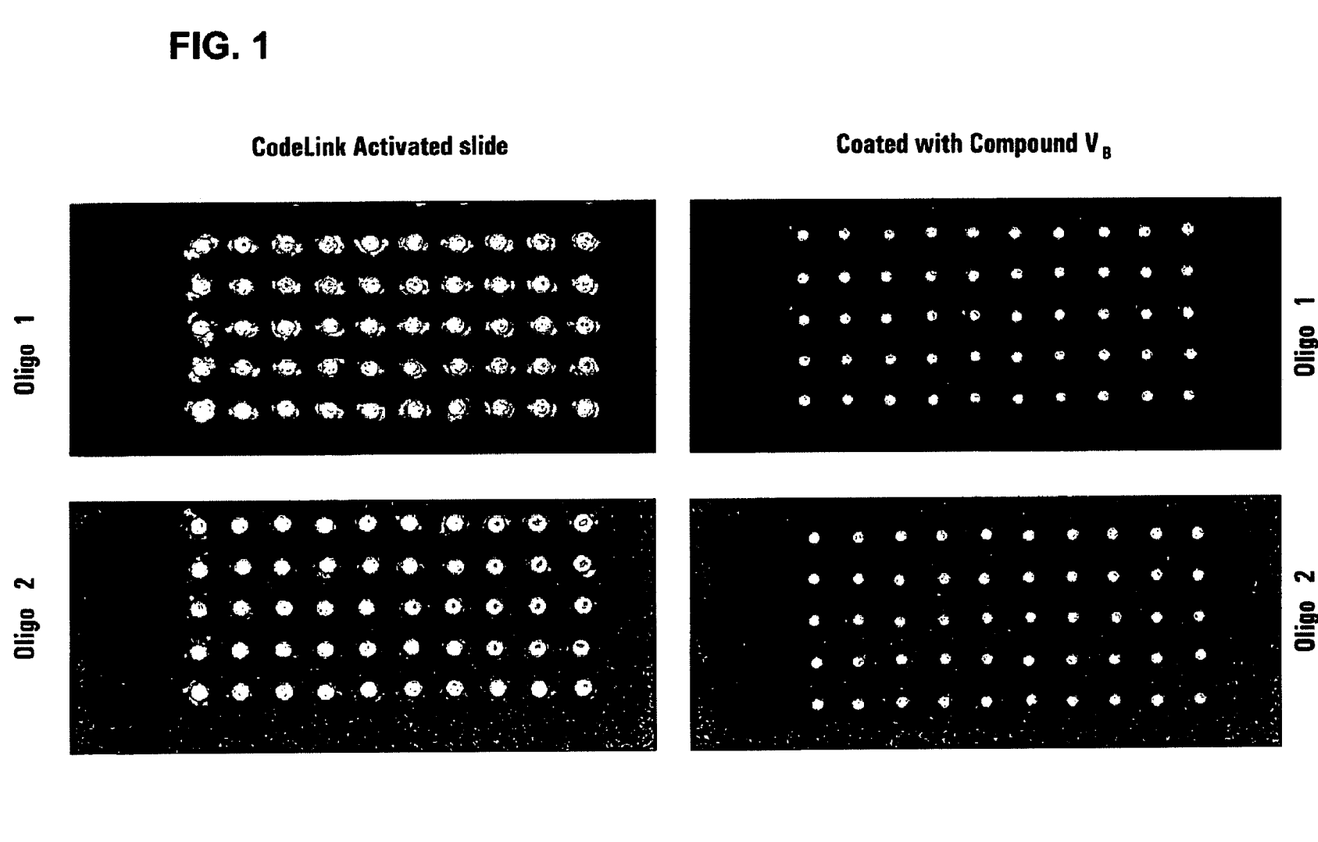
FIG. 1 presents images of spots printed on a conventional surface and a surface coated with a polymer according to the present invention (Compound $V_B$). Slides were printed with Oligo 1 and 2 and processed as described in Example 7

The results listed in Table 3 show that the coatings with different compositions of Compound V (Table 2) produce spots of diameter 55 to 58 microns from oligo immobilization and signal intensity of 20,672 to 29,753 fluorescent units from Oligo 1 (FIG. 1). Spot sizes measured from slides printed with Oligo 2 were 63 to 69 microns and signal intensity of 9,938 to 12,277 fluorescent units. Contact angle from these slides varied between 41° and 44°. Conventional slides, for example, CodeLink Activated slides (Amersham Biosciences, Piscataway, N.J.) produced, under the same conditions, spots of 99 and 102 microns diameter with Oligo 1 and Oligo 2 respectively. Signal intensity from these spots was 21,293 and 6,760 fluorescent units from Oligo 1 and Oligo 2 respectively. Contact angle was 19.8°. These results demonstrate that the DMA polymer backbone produces a highly desirable surface for printing high density microarrays.

TABLE 3

| Compounds | Contact Angle (°) | Oligo 1 | | Oligo 2 | |
|---|---|---|---|---|---|
| | | Spot Size (µ) | Signal Intensity (Fluorescent Units) | Spot Size (µ) | Signal Intensity (Fluorescent Units) |
| $V_A$ | 42.0 | 55.4 | 23,363.3 | 63.3 | 10,269.3 |
| $V_B$ | 41.8 | 57.7 | 25,759.3 | 68.5 | 10,726.6 |
| $V_C$ | 44.3 | 56.0 | 29,338.3 | 64.0 | 9,938.8 |
| $V_D$ | 41.0 | 56.3 | 24,545.5 | 66.4 | 10,916.1 |
| $V_E$ | 44.1 | 56.3 | 26,758.8 | 64.3 | 10,004.8 |
| $V_F$ | 41.5 | 56.4 | 28,042.8 | 68.0 | 10,715.8 |
| $V_G$ | 41.5 | 57.8 | 27,232.3 | 67.9 | 12,277.9 |
| $V_H$ | 41.0 | 58.1 | 20,671.8 | 65.9 | 10,539.7 |
| $V_I$ | 42.9 | 55.6 | 29,753.8 | 64.4 | 10,273.6 |
| CodeLink ™ | 19.8 | 98.9 | 21,293.0 | 101.5 | 6,760.5 |

CodeLink ™ is a trademark of Amersham BioSciences.

Example 8

Preparation of N-(3-isothiocyanatopropyl)-2-methylacrylamide (APMA-NCS) (Compound VI)

In a 500 ml round bottom flask fitted with an overhead stirrer, a thermocouple, drying tube, and an addition funnel; was placed APMA-HCl (20.0 g, 112 mmole; Compound II) and chloroform (100 ml; CHCl$_3$). Then carbon disulfide (9.84 g [7.46 ml], 19.2 mmole; CS$_2$) was added in about 5 minutes; followed by the addition of triethylamine (11.32 g [15.6 ml], 111.8 mmole). The reaction was cooled in an ice bath to 3 to 8° C. To the cooled solution was added a solution of dicyclohexylcarbodiimide (25.8 g, 125.0 mmole; DCC) in CHCl$_3$ (40 ml) over a period of 30 minutes using the addition funnel. The reaction was stirred using the ice bath for 1 hour after the addition was complete. The reaction was then stirred at room temperature over night. The solvent was removed using a rotary evaporator with an air bleed. The 75.6 g residue was flash purified using two 76.2 mm (3 in.) in diameter by 215.9 mm (8.5 in.) long silica gel columns eluted with a gradient of acetone/chloroform-4/96 to 6/94. There were 92-50 ml fractions collected from each column.

The product was found in fractions 39-92 by TLC (thin layer chromatography) (acetone/chloroform-10/90). The combined fractions were evaporated and extracted with 3×50 ml of hexane. The solvent was removed to give 12.5 g of residue, which was flash purified again using a 76.2 mm (3 in.) in diameter by 203.2 mm (8 in.) long silica gel column. The column was eluted with 72×25 ml fractions of acetone/chloroform-5/95 followed by eluting fractions 73-145 (25 ml) using acetone/chloroform-10/90. Evaporation of fractions 73-140 gave 11.5 g of Compound VI, which was a single spot by TLC Also the analysis on a 400 MHz NMR spectrometer was consistent with the desired product: $^1$H NMR (CDCl$_3$) amide proton 6.37 (broad s, 1H), vinyl protons at 5.70 (s, 1H) and 5.34 (s, 1H), methylene protons adjacent to nitrogen 3.60 and 3.42 (m, 4H), and the methyl protons combined with the central methylene protons 1.95 (m, 5H). Compound VI was used to prepare Compound VII, Comparative Compound VIII, and Compound XI.

Example 9

Preparation of N-[3-({[(2,2-dimethoxyethyl)amino]carbonothioyl}amino)propyl]-2-methylacrylamide (DME-APMA) (Compound VII)

In a 20 ml vial was placed APMA-NCS (Compound VI) 1.93 g, 10.5 mmole; (2,2-dimethoxyethyl)amine 1.06 g, 10.0 mmole; and chloroform 7 ml. The reaction was stirred at room temperature over night. TLC indicated the presence of starting materials. The reaction was heated to 50° C. for 4 hours. The reaction was nearly complete, and it was allowed to stir at 50° C. overnight. The solvent was evaporated to give 3.07 g of white solid. The crude product was flash purified on a 41.3 mm (1⅝ in.) diameter silica gel column 152 mm (6 in.) long. The column was eluted with 3 L of acetone/chloroform-30/70 with 33 ml fractions. Fractions 26-78 were combined and evaporated to give 2.73 g (94% of theory) of Compound VII. Analysis on a 400 MHz NMR spectrometer was consistent with the desired dimethoxyethyl-APMA: $^1$H NMR (CDCl$_3$) amide protons 7.23, 7.02 and 6.5 (broad s, 3H); vinyl protons at 5.81 (s, 1H) and 5.37 (s, 1H); methyne proton 4.47 (t, 1H); methylene protons 3.7 (m, 2H), 3.62 (m, 2H), and 3.36 (m, 2H); methoxy protons 3.42 (s, 6H); methyl proton 1.99 (m, 3H); and the central methylene 1.75 (m, 2H). Compound VII was used to prepare Comparative Compound XII and Compound XIII.

Example 10

Preparation of a copolymer of acrylamide, BBA-APMA, and APMA-NCS (Photo-PA-NCS)(Comparative Compound VIII)

A photoactivatable copolymer was prepared in the following manner. Acrylamide, 0.42 g (5.92 mmol), Compound III, prepared according to the general method described in Example 3, 0.016 g (0.046 mmol), Compound VI, 0.064 g (0.347 mmol), and Vazo-67 0.014 g (0.073 mmol) were dissolved in 5.5 ml of tetrahydrofuran (THF). The THF solution was sparged with helium for 4 minutes; then the reaction solution was blanketed with nitrogen and placed in an oven at 50° to 55° C. overnight. The polymer was isolated by filtration. The solid was washed with 2×5 ml of THF. The product was dried under vacuum at 30° C. to give 0.44 g of a white solid (Comparative Compound VIII). A procedure similar to the one above was used to prepare Comparative Compound XII as shown below in Table 4.

Example 11

Preparation of a copolymer of acrylamide, BBA-APMA, and Glycidyl methacrylate (GMA) (Photo-PA-Epoxide) (Comparative Compound IX)

A photoactivatable copolymer was prepared in the following manner. Acrylamide, 14.1 g (199 mmol), Compound III, prepared according to the general method described in Example 3, 0.829 g (2.37 mmol), GMA, 5.04 g (35.5 mmol), and Vazo-67 0.43 g (2.24 mmol) were dissolved in 200 ml of tetrahydrofuran (THF). The THF solution was added to a second stirred refluxing solution of Vazo-67 0.116 g (0.60 mmol) in THF (50 ml) under an inert atmosphere over one hour. The solution was refluxed 4 hours with stirring under an inert atmosphere. The polymer was isolated by filtration. The solid was washed with 2×80 ml of THF. The product was dried under vacuum at 30° C. to give 19.6 g of a white solid (Comparative Compound IX).

Example 12

Preparation of Copolymer of (DMA), BBA-APMA, and (GMA) (Photo-DMA-Epoxide) (Compound X)

A photoactivatable copolymer was prepared in the following manner. DMA, 7.70 g (77.7 mmol), Compound III, prepared according to the general method described in Example 3, 0.324 g (0.925 mmol), GMA (Sigma, St. Louis, Mo.) 1.97 g (13.9 mmol), Vazo-67 0.189 g (0.983 mmol) were dissolved in 68. ml of THF. The THF solution was sparged with helium for 4 minutes; then the reaction solution was blanketed with nitrogen and placed in an oven at 50° to 55° C. overnight. The polymer was isolated by slow addition of the THF solution to vigorously stirred diethyl ether (500 ml). The precipitated polymer product was isolated by filtration and the filter cake was rinsed thoroughly with 2×50 ml ether. The product was dried under vacuum at 30° C. to give 9.6 g of a white solid (Compound X)

A procedure similar to the one above was used to prepare compounds Compound XI, Compound XIII, and Compound XIV(Acryloylmorpholine can be purchased from Sigma Aldrich, St. Louis, Mo.) as shown below in Tables 4 and 5.

Example 13

Production of Slides Coated with Dimethyl Acrylamide Polymer Using Alternate Reactive Chemistry Soda lime microscope glass slides (Erie Scientific, Portsmouth, N.H.) were silane treated by dipping in a mixture of N-decyldimethylchlorosilane and p-tolyldimethylchlorosilane (United Chemical Technologies, Bristol, Pa.) 1% each in acetone, for one minute. After air drying, the slides were cured in an oven at 110° C. for a minimum of 30 minutes. Slides were then washed with acetone followed by dipping in DI water. Finally, the slides were further dried in an oven for 10 minutes at 110° C.

Silane treated slides were then coated with a polymer composition by a variation of known methods. For example, the 6 Compounds in Table 4 were sprayed at 2 mg/ml onto the silane treated slides, which were then illuminated using a Dymax Lamp (25 mjoule/cm$^2$ as measured at 335 nm with a 10 nm band pass filter on an International Light radiometer) while wet, washed with deionized water, and dried. Oligonucleotides were printed on these slides using a home made arrayer that used capillary dispensing pins (0.004" i.d.)(Norlico Corporation, Hampton Falls, N.H.). An oligonucleotide with an amine on the 5' and TAMRA dye on the 3' end was printed. The sequence was GCC ATG TGC AGT CTG GTT CAG GTT CAT AAA (SEQ ID NO:1). The oligo was prepared at a 20 uM concentration in 50 mM sodium phosphate buffer at pH 8.5. Immediately after printing, slides were placed overnight in a sealed sodium chloride chamber to maintain 75% relative humidity. The printed slides were then washed with a pre-warmed solution of 50 mM ethanolamine in 0.1 M Tris, pH 9.0 (Sigma, St. Louis, Mo.) at 45° C. for 30 minutes followed by another wash in pre-warmed 0.1% N-lauryl sarcosine (Sigma, St. Louis, Mo.) in 5×SSC (75 mM sodium citrate, 0.75 M sodium chloride) for 1.5 hours at 45° C. Finally the slides were soaked in 10 mM citrate buffer at room temperature for 15 minutes and centrifuged to dry. Slides were scanned on GenePix 4000B microarray scanner (Axon Instruments, Union City, Calif.). Table 4 summarizes the results.

TABLE 4

| | | Monomer mole % | | | | | |
|---|---|---|---|---|---|---|---|
| | | The remainder is the backbone monomer. | | | | | |
| Compound # | Monomer of the Polymer Backbone | Photo (BBA-APMA) | Epoxide (GMA) | Isothiocyanate (APMA-NCS) | Aldehyde (DME-APMA) | Spot Size (μ) | Signal Intensity (Fluorescent Units) |
|---|---|---|---|---|---|---|---|
| Comparative-VIII | Acrylamide | 0.72 | 0.00 | 5.50 | 0.00 | 414 | 6004 |
| Comparative-IX | Acrylamide | 1.00 | 15.0 | 0.00 | 0.00 | 329 | 15679 |
| X | N,N-dimethyl acrylamide | 1.00 | 15.0 | 0.00 | 0.00 | 174 | 12068 |
| XI | N,N-dimethyl acrylamide | 1.00 | 0.00 | 7.50 | 0.00 | 176 | 5253 |
| Comparative-XII | Acrylamide | 1.00 | 0.00 | 0.00 | 20.0 | 271 | 1702 |
| XIII | N,N-dimethyl acrylamide | 1.00 | 0.00 | 0.00 | 20.0 | 178 | 1422 |

Example 14

Production of Slides Coated with Polymer Using an Acryloylmorpholine Backbone

Soda lime microscope glass slides (Erie Scientific, Portsmouth, N.H.) were silane treated by dipping in a mixture of N-decyldimethylchlorosilane and p-tolyldimethylchlorosilane (United Chemical Technologies, Bristol, Pa.) 1% each in acetone, for one minute. After air drying, the slides were cured in an oven at 110° C. for a minimum of 30 minutes. Slides were then washed with acetone followed by dipping in DI water. Finally, the slides were further dried in an oven for 10 minutes at 110° C.

Silane treated slides were then coated with the polymer composition by a variation of known methods. Compound XIV at 2 mg/ml, was sprayed onto the silane treated slides, which was then illuminated using a Dymax Lamp (25 mjoule/cm$^2$ as measured at 335 nm with a 10 nm band pass filter on an International Light radiometer) while wet, washed with deionized water, and dried. Oligonucleotides were printed on these slides using a home made arrayer that used capillary dispensing pins 0.152 mm (0.006") i.d., Norlico Corporation). An oligonucleotide with an amine on the 3' and Cy3 dye on the 5' end was printed. The sequence was GTC TGA GTC GGA GCC AGG GCG GCC GCC AAC (SEQ ID NO:2). The oligo was prepared at a 20 uM concentration in 50 mM sodium phosphate buffer at pH 8.5. Immediately after printing, slides were placed overnight in a sealed sodium chloride chamber to maintain 75% relative humidity. The printed slides were then washed with a pre-warmed solution of 50 mM ethanolamine in 0.1 M Tris, pH 9.0 (Sigma, St. Louis, Mo.) at 45° C. for 30 minutes followed by another wash in pre-warmed 0.1% N-lauryl sarcosine (Sigma, St. Louis, Mo.) in 5×SSC (75 mM sodium citrate, 0.75 M sodium chloride) for 1.5 hours at 45° C. Finally the slides were soaked in 10 mM citrate buffer at room temperature for 15 minutes and centrifuged to dry. Slides were scanned on GenePix 4000B microarray scanner (Axon Instruments, Union City, Calif.). In addition, contact angle of the spot on the substrate was measured. Contact angle data was collected on a Krüss DSA MK2 goniometer (Krüss, Hamburg, Germany) and calculated using the Fowkes method. Table 5 summarizes the results.

TABLE 5

| Surface | Monomer of the Polymer backbone | Photo (BBA-APMA) | NOS (Mal-EAC-NOS) | Spot Size (μ) | Signal Intensity (Fluorescent Units) | Contact Angle (°) |
|---|---|---|---|---|---|---|
| Compound XIV | N-acryloyl morpholine*$_1$ | 1.80 | 13.70 | 326 | 16792 | 46.0 |
| CodeLink ™ | | | | 508 | 15229 | 19.8 |

*$_1$N-acryloylmorpholine can be purchased from Sigma-Aldrich (St. Louis, MO)
CodeLink ™ is a trademark of Amersham BioSciences.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "adapted and configured" describes a system, apparatus, or other structure that is constructed or configured to perform a particular task or adopt a particular configuration to. The phrase "adapted and configured" can be used interchangeably with other similar phrases such as arranged and configured, constructed and arranged, adapted, constructed, manufactured and arranged, and the like.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

What is claimed is:

1. A substrate comprising a surface and a polymer, the polymer coating at least a portion of the surface;
the polymer comprising:
at least about 40 mol-% of monomer comprising an uncharged polar moiety other than primary amide; and
one or more pendent reactive groups configured to form covalent bond with biomolecule, wherein one or more pendent reactive groups are selected from thermochemically reactive groups, photo reactive groups, or mixtures thereof.

2. The substrate of claim 1, wherein the polymer comprises:
N-substituted acrylamide, N,N-disubstituted acrylamide, N-substituted methacrylamide, N,N-disubstituted methacrylamide, or mixture thereof;
hydroxyalkylacrylate, hydroxyalkylmethacrylate, alkyl or aryl acrylate, alkyl or aryl methacrylate, ethoxyethoxyethylacrylate, polypropyleneglycolmonomethacrylate, or mixtures thereof;
vinylpyrrolidone, vinylcaprolactam, N-vinyl-N-methylacetamide, vinylmethylether, 2-vinylpyridine-N-oxide, vinylmethylsulfone, or mixtures thereof;
ethyleneglycol, ethyleneimine, PEG derivative of mono methacrylate, or mixtures thereof;
aminimide; or mixtures thereof.

3. A substrate comprising:
support surface; and
polymer coupled to the support surface; the polymer comprising:
at least about 40 mol-% of monomer comprising an uncharged polar moiety other than primary amide; and
more than one reactive group selected from thermochemically reactive groups, photo reactive groups, or mixtures thereof;
wherein the polymer is configured to form covalent bonds with biomolecule.

4. A composition comprising polymer;
the polymer comprising:
at least about 40 mol-% of monomer comprising an uncharged polar moiety other than primary amide; and
one or more reactive groups configured to form covalent bonds with corresponding functional groups on biomolecule, wherein one or more pendent reactive groups are selected from thermochemically reactive groups, photo reactive groups, or mixtures thereof;
the polymer being configured to be covalently attached to surface.

5. The composition of claim 4, wherein the polymer comprises:
N-substituted acrylamide, N,N-disubstituted acrylamide, N-substituted methacrylamide, N,N-disubstituted methacrylamide, or mixture thereof;
hydroxyalkylacrylate, hydroxyalkylmethacrylate, alkyl or aryl acrylate, alkyl or aryl methacrylate, ethoxyethoxyethylacrylate, polypropyleneglycolmonomethacrylate, or mixtures thereof;
vinylpyrrolidone, vinylcaprolactam, N-vinyl-N-methylacetamide, vinylmethylether, 2-vinylpyridine-N-oxide, vinylmethylsulfone, or mixtures thereof;
ethyleneglycol, ethyleneimine, PEG derivative of monomethacrylate, or mixtures thereof;
aminimide; or
mixtures thereof 6. The composition of claim 4, wherein the polymer coating comprises a monomer comprising an uncharged polar moiety other than primary amide in an amount effective to provide, when coated on a surface of a substrate, a contact angle of about 30° to about 60° for a sessile water drop.

7. A micro array comprising:
support surface;
polymer covalently coupled to the support surface;
the polymer comprising:
at least about 40 mol-% of monomer comprising an uncharged polar moiety other than primary amide; and one or more reactive groups selected from thermochemically reactive groups, photo reactive groups, or mixtures thereof;

biomolecule covalently bound to the polymer in discrete spots.

8. The micro array of claim 7, wherein the polymer comprises:

N-substituted acrylamide, N,N-disubstituted acrylamide, N-substituted methacrylamide, N,N-disubstituted methacrylamide, or mixture thereof;

hydroxyalkylacrylate, hydroxyalkylmethacrylate, alkyl or aryl acrylate, alkyl or aryl methacrylate, ethoxyethoxyethylacrylate, polypropyleneglycolmonomethacrylate, or mixtures thereof;

vinylpyrrolidone, vinylcaprolactam, N-vinyl-N-methylacetamide, vinylmethylether, 2-vinylpyridine-N-oxide, vinylmethylsulfone, or mixtures thereof;

ethyleneglycol, ethyleneimine, PEG derivative of monomethacrylate, or mixtures thereof;

aminimide; or mixtures thereof.

9. The microarray of claim 7, wherein the polymer coating comprises a monomer comprising an uncharged polar moiety other than primary amide in an amount effective to provide a contact angle of about 30° to about 60° for a sessile water drop.

* * * * *

SEQUENCE LISTING

<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: Synthetic

<400> SEQUENCE: 1
gccatgtgca gtctggttca ggttcataaa 30

<210> SEQ ID NO 2
<211> LENGTH: 30
<212> TYPE: DNA
<213> ORGANISM: Artificial Sequence
<220> FEATURE:
<223> OTHER INFORMATION: Synthetic

<400> SEQUENCE: 2
gtctgagtcg gagccagggc ggccgccaac 30